United States Patent
Wakeford

(10) Patent No.: US 11,625,826 B2
(45) Date of Patent: Apr. 11, 2023

(54) RETINAL OCT DATA PROCESSING

(71) Applicant: Optos Plc, Dunfermline (GB)

(72) Inventor: Peter Robert Wakeford, Dunfermline (GB)

(73) Assignee: OPTOS PLC, Dunfermline (GB)

( * ) Notice: Subject to any disclaimer, the term of this patent is extended or adjusted under 35 U.S.C. 154(b) by 241 days.

(21) Appl. No.: 17/062,999

(22) Filed: Oct. 5, 2020

(65) Prior Publication Data

US 2021/0110537 A1 Apr. 15, 2021

Related U.S. Application Data

(63) Continuation-in-part of application No. 16/595,052, filed on Oct. 7, 2019.

(51) Int. Cl.

| | |
|---|---|
| G06T 7/00 | (2017.01) |
| G06T 7/13 | (2017.01) |
| A61B 3/10 | (2006.01) |
| G06T 7/11 | (2017.01) |
| G06T 7/143 | (2017.01) |

(Continued)

(52) U.S. Cl.
CPC .......... G06T 7/0012 (2013.01); A61B 3/0025 (2013.01); A61B 3/102 (2013.01); A61B 3/1225 (2013.01); G06N 3/08 (2013.01); G06T 7/11 (2017.01); G06T 7/13 (2017.01); G06T 7/143 (2017.01); G16H 30/20 (2018.01);

(Continued)

(58) Field of Classification Search
CPC ..... A61B 3/102; A61B 3/0025; A61B 3/1225; G06T 7/0012; G06T 7/11; G06T 2207/10101; G06T 2207/30041; G06T 7/143; G06T 7/181; G06T 2207/20076; G06T 5/20; G06T 7/12; G06N 3/08; G06N 5/003; G06N 7/005; G16H 30/20; G16H 30/40

See application file for complete search history.

(56) References Cited

U.S. PATENT DOCUMENTS

| 2012/0134563 A1 | 5/2012 | Nakano |
| 2018/0092528 A1* | 4/2018 | Takeno ................ A61B 3/0025 |

OTHER PUBLICATIONS

Li et al., "Integrating Handcrafted and Deep Features for Optical Coherence Tomography Based Retinal Disease Classification", IEEE Access, vol. 7, pp. 33771-33777 (2019).

(Continued)

*Primary Examiner* — Jon Chang
(74) *Attorney, Agent, or Firm* — DeLucia, Mlynar & Associates LLP

(57) ABSTRACT

A method of method of processing optical coherence tomography, OCT, image data representing an OCT image of a retina of an eye, to generate mapping data which maps out a predetermined band of a plurality of distinct bands which extend across the OCT image and correspond to respective anatomical layers of the retina. The method comprises: receiving the OCT image data; processing A-scan data of the received OCT image data to generate data indicative of sequences of A-scan elements corresponding to the predetermined band of the plurality of distinct bands and having respective A-scan element values that vary in accordance with a predetermined pattern; and generating the mapping data by applying a line-finding algorithm to determine a line passing through the sequences of A-scan elements indicated by the generated data.

30 Claims, 11 Drawing Sheets

(51) Int. Cl.
A61B 3/00 (2006.01)
A61B 3/12 (2006.01)
G16H 30/20 (2018.01)
G06N 3/08 (2023.01)
(52) U.S. Cl.
CPC .............. *G06T 2207/10101* (2013.01); *G06T 2207/30041* (2013.01)

(56) References Cited

OTHER PUBLICATIONS

Gholami et al., "Intra-Retinal Segmentation of Optical Coherence Tomography Images Using Active Contours with a Dynamic Programming Initialization and an Adaptive Weighted Strategy", Proceedings of SPIE vol. 10483, pp. 104832M-1 to 104832M-6 (2018).
Office Action dated Jun. 9, 2022 in U.S. Appl. No. 16/595,052.
Joe Bayley et al., SOAP: A generalized application of the Viterbi algorithm to searches for continuous gravitational-wave signals, Phys. Rev. D, vol. 100, Issue 2, pp. 1-16 (2019).
J. Bayley et al.,"Generalized application of the Viterbi algorithm to searches for continuous gravitational-wave signals" J Phys. R.,ev.D, vol. 100, Issue 2 (Jul. 15, 2019).
"Atlas of OCT" by Adams, N.A., Heidelberg Engineering, 2013, 39 pages.

* cited by examiner

RETINAL OCT DATA PROCESSING

CROSS REFERENCE TO RELATED APPLICATION

This application is a continuation-in-part (CIP) of U.S. application Ser. No. 16/595,052, filed Oct. 7, 2019, and claims the benefit of priority of that application. U.S. application Ser. No. 16/595,052 is incorporated by reference herein in its entirety, as if set forth fully herein.

TECHNICAL FIELD

Example aspects herein generally relate to the field of optical coherence tomography (OCT) data processing and, more particularly, to the processing of OCT image data representing an OCT image of a retina of an eye, to map out a predetermined layer of the retina in the OCT image.

BACKGROUND

Optical coherence tomography provides a powerful tool for examining and assessing the health of the retina of an eye. Being able to automatically and accurately map out or trace, across an OCT image of the retina, a specific retinal layer of interest from among the different layers of the retina that are discernible in the OCT image, would greatly facilitate OCT image analysis and may allow useful information on the retina to be obtained.

FIGS. 1a and 1b (from "Atlas of OCT" by Adams, N. A., Heidelberg Engineering) illustrate an example OCT B-scan image of a retina (FIG. 1a), and an enlarged segment (FIG. 1b) of the OCT B-scan image. A grey-scale enhancement of the enlarged segment is shown on the left-hand side of FIG. 1b. Up to 18 distinct layers are typically visible in an OCT B-scan image of a retina, and a mapping of some of these layers to associated anatomical layers of the retina (including the Inner/Outer Segment (IS/OS junction layer)) is shown in FIG. 1b.

It is known to use image classification algorithms, such as Convolutional Neural Network (CNN)-based segmentation, to automatically segment an OCT retinal image into distinct retinal layers.

SUMMARY

The process of training a CNN is typically a slow and resource-intensive task. In order to achieve effective CNN-based segmentation, the CNN typically has to be trained on a large number of images. Furthermore, if a CNN has been configured to segment OCT images acquired by a given OCT imaging system, a switch to processing OCT data from a second, different OCT imaging system will normally require the CNN to be retrained using images acquired by the second OCT imaging system.

In view of the above shortcomings of conventional approaches to identifying one or more retinal layers in an OCT retinal image through image segmentation, the present inventor has devised, in accordance with at least some of the example embodiments herein, a fast and computationally efficient way of automatically mapping out one or more retinal layers in an OCT retinal image.

In more detail, there is provided, in accordance with a first example aspect herein, a method of processing optical coherence tomography, OCT, image data representing an OCT image of a retina of an eye, to generate mapping data which maps out a predetermined band of a plurality of distinct bands which extend across the OCT image and correspond to respective anatomical layers of the retina. The method comprises receiving the OCT image data; processing A-scan data of the received OCT image data to generate data indicative of sequences of A-scan elements corresponding to the predetermined band of the plurality of distinct bands and having respective A-scan element values that vary in accordance with a predetermined pattern; and generating the mapping data by applying a line-finding algorithm to determine a line passing through the sequences of A-scan elements indicated by the generated data.

By way of a non-limiting example, since photoreceptor outer segments of a retina are typically visible as a thin grey band between brighter white bands in an OCT B-scan image of the retina (as illustrated in FIG. 1b), this particular variation in pixel intensity in an A-scan direction can be searched for by correlating the OCT image with a kernel which is appropriately configured to accentuate this particular band of interest. A line detection algorithm can then be applied to a result in order to map out the band across at least a part of the OCT B-scan image. The resulting mapping may be useful to guide subsequent image processing operations (e.g. layer brightness and/or thickness analysis) or may alternatively be displayed to a medical practitioner on any suitable display device (e.g. an LCD screen or the like) to facilitate identification of the layer for retinal health assessment, for example.

There is also provided, in accordance with a second example aspect herein, an image processing apparatus configured to process OCT image data representing an OCT image of a retina of an eye, to generate mapping data which maps out a predetermined band of a plurality of distinct bands which extend across the OCT image and correspond to respective anatomical layers of the retina. The image processing apparatus comprises a receiver module configured to receive the OCT image data, and an A-scan processing module configured to process A-scan data of the received OCT image data to generate data indicative of sequences of A-scan elements corresponding to the predetermined band of the plurality of distinct bands and having respective A-scan element values that vary in accordance with a predetermined pattern. The image processing apparatus further comprises a mapping module configured to generate the mapping data by applying a line-finding algorithm to determine a line passing through the sequences of A-scan elements indicated by the generated data.

There is also provided, in accordance with a third example aspect herein, a non-transitory computer-readable storage medium storing computer program instructions which, when executed by a computer, cause the computer to perform a method of processing OCT image data representing an OCT image of a retina of an eye, to generate mapping data which maps out a predetermined band of a plurality of distinct bands which extend across the OCT image and correspond to respective anatomical layers of the retina. The method comprises: receiving the OCT image data; processing A-scan data of the received OCT image data to generate data indicative of sequences of A-scan elements corresponding to the predetermined band of the plurality of distinct bands and having respective A-scan element values that vary in accordance with a predetermined pattern; and generating the mapping data by applying a line-finding algorithm to determine a line passing through the sequences of A-scan elements indicated by the generated data.

BRIEF DESCRIPTION OF THE DRAWINGS

Example embodiments will now be explained in detail, by way of non-limiting example only, with reference to the accompanying figures described below. Like reference numerals appearing in different ones of the figures can denote identical or functionally similar elements, unless indicated otherwise.

FIG. 1b shows an enlarged and partially enhanced segment of the OCT B-scan image of FIG. 1a.

DETAILED DESCRIPTION OF EXAMPLE EMBODIMENTS

Example embodiments herein will now be described in more detail with reference to the accompanying drawings.

Figure 2:
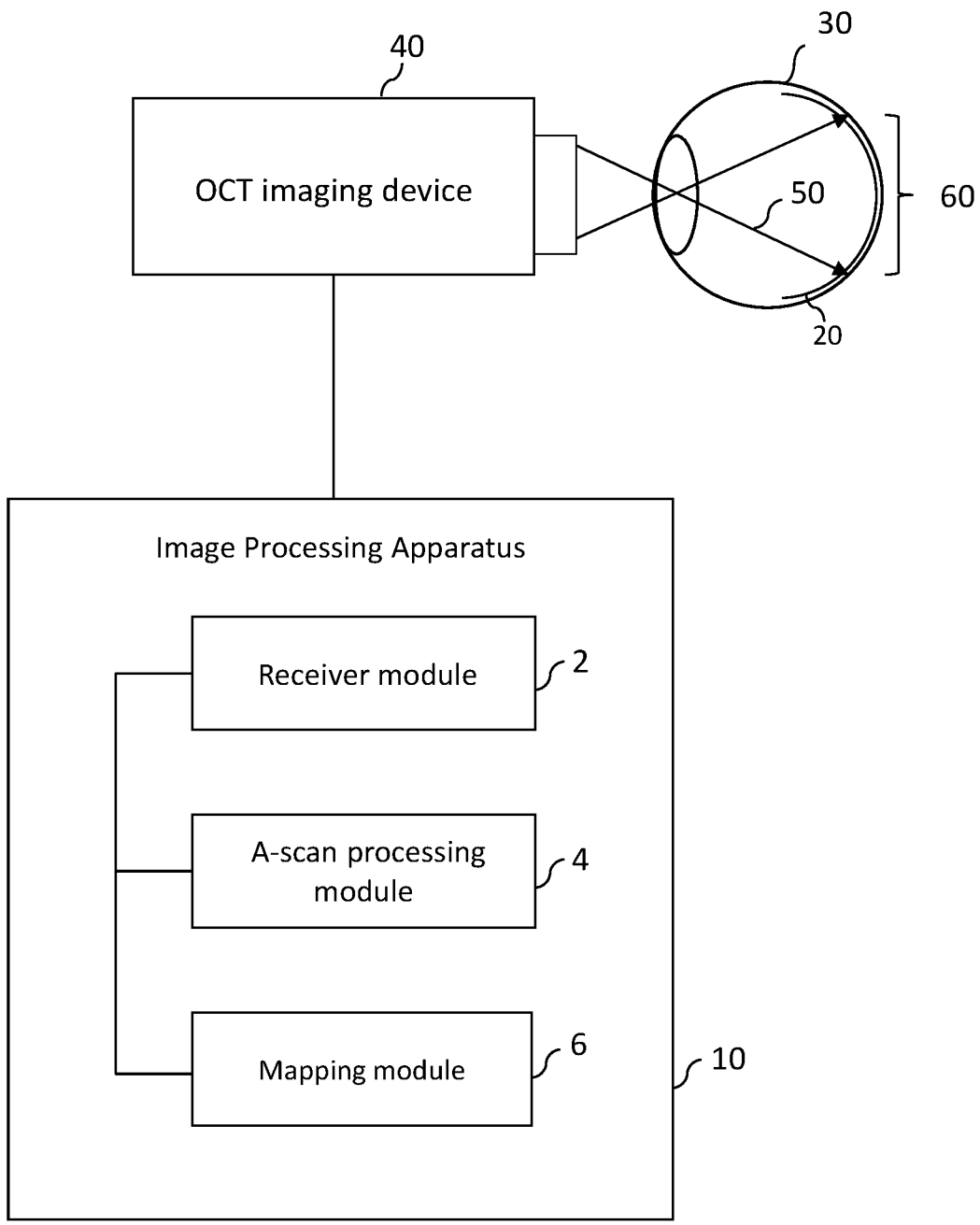
FIG. 2 is a schematic illustration of an image processing system for processing OCT image data according to a first example embodiment herein.

FIG. 2 is a schematic illustration of an image processing apparatus 10 according to an example embodiment. The image processing apparatus 10 is configured to process OCT image data representing an OCT image of a retina 20 of an eye 30, to generate mapping data which maps out a predetermined band of a plurality of distinct bands which extend across the OCT image and correspond to respective anatomical layers of the retina 20. The OCT image data processed by the image processing apparatus 10 is acquired by an OCT imaging device 40 that employs an ophthalmic scanner to scan an OCT sample beam 50 across a region 60 of the retina 20. The image processing apparatus 10 may, as in the present example embodiment, be provided as an apparatus that is separate from the OCT imaging device 40.

The image processing apparatus 10 may alternatively form part of the OCT imaging device 40. The OCT imaging device 40 may be any kind of OCT scanner well-known to those skilled in the art, which is capable of acquiring retinal OCT data from the subject's eye 30. The retinal OCT data may be in the form of B-scans and/or C-scans, wherein each B-scan or C-scan comprises A-scan data of A-scans that have been acquired by the OCT scanner at respective scan locations on the retina 20.

As illustrated in FIG. 2, the image processing apparatus 10 of the present example embodiment comprises a receiver module 2 configured to receive the OCT image data generated by the OCT imaging device 40. The receiver module 2 may, as in the present example embodiment, receive the OCT image data directly from the OCT imaging device 40 via a dedicated data link, or alternatively indirectly, via a network such as a Local Area Network (LAN) or the Internet, for example. As a further alternative, the receiver module 2 may acquire the OCT image data by reading a computer storage medium, such as a CD, DVD or flash drive, for example, having the OCT image data stored therein.

The image processing apparatus 10 further comprises an A-scan processing module 4 configured to process the A-scan data in the received OCT image data to generate data that is indicative of sequences of A-scan elements corresponding to the predetermined one of the plurality of distinct bands and having respective A-scan element values that vary in accordance with a predetermined pattern.

Furthermore, the image processing apparatus 10 comprises a mapping module 6, which is configured to generate the mapping data by applying a line-finding algorithm to determine a line passing through the sequences of A-scan elements indicated by the generated data.

Figure 3:
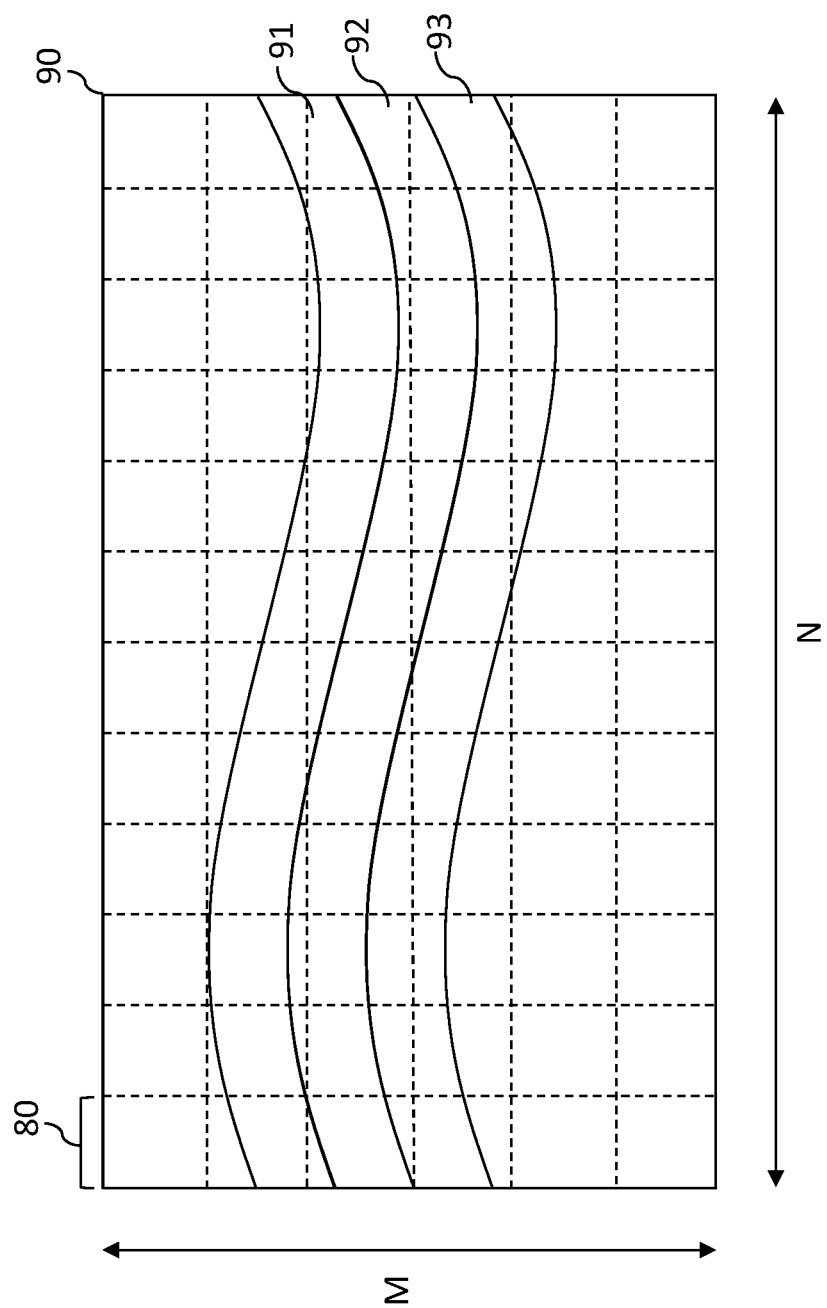
FIG. 3 is a schematic illustration of an OCT B-scan comprising a plurality of OCT A-scans.

FIG. 3 is an illustration of a sequence of OCT A-scans 80 forming an OCT B-scan 90 which is received by the receiver module 2. The B-scan 90 is represented by an M×N element array, and comprises an integer number N of A-scans 80, where each A-scan 80 is represented by an M×1 element array that comprises an integer number M of A-scan elements. Each A-scan element has a corresponding A-scan element value associated with it. An A-scan 80 is generated by directing the OCT sample beam 50 to a point on the surface of the retina 20 and combining light of the reflected OCT sample beam with an OCT reference beam within the OCT imaging device 40 to form an interference pattern from which a one-dimension section through the retina 20 can be obtained. In FIG. 3, each A-scan 80 is represented by a column of elements in the OCT B-scan 90. By displacing one of the retina 20 and the OCT sample beam 50 relative to the other between each acquisition of an A-scan, a sequence of A-scans 80 is generated and concatenated by the OCT imaging device 40 to form the B-scan 90, which provides a two-dimensional cross-sectional view of the retina 20. Similarly, in an example embodiment in which the OCT imaging device 40 performs an OCT scan over/across a two-dimensional region of the retina 20, a sequence of OCT B-scans 90 is acquired, the acquired B-scans 90 collectively form an OCT C-scan that provides a three-dimensional image of part of the retina 20. As illustrated schematically in FIG. 3, the B-scan image shows a plurality of bands 91, 92 and 93, each corresponding to a different respective layer of the retina 20.

Figure 4:
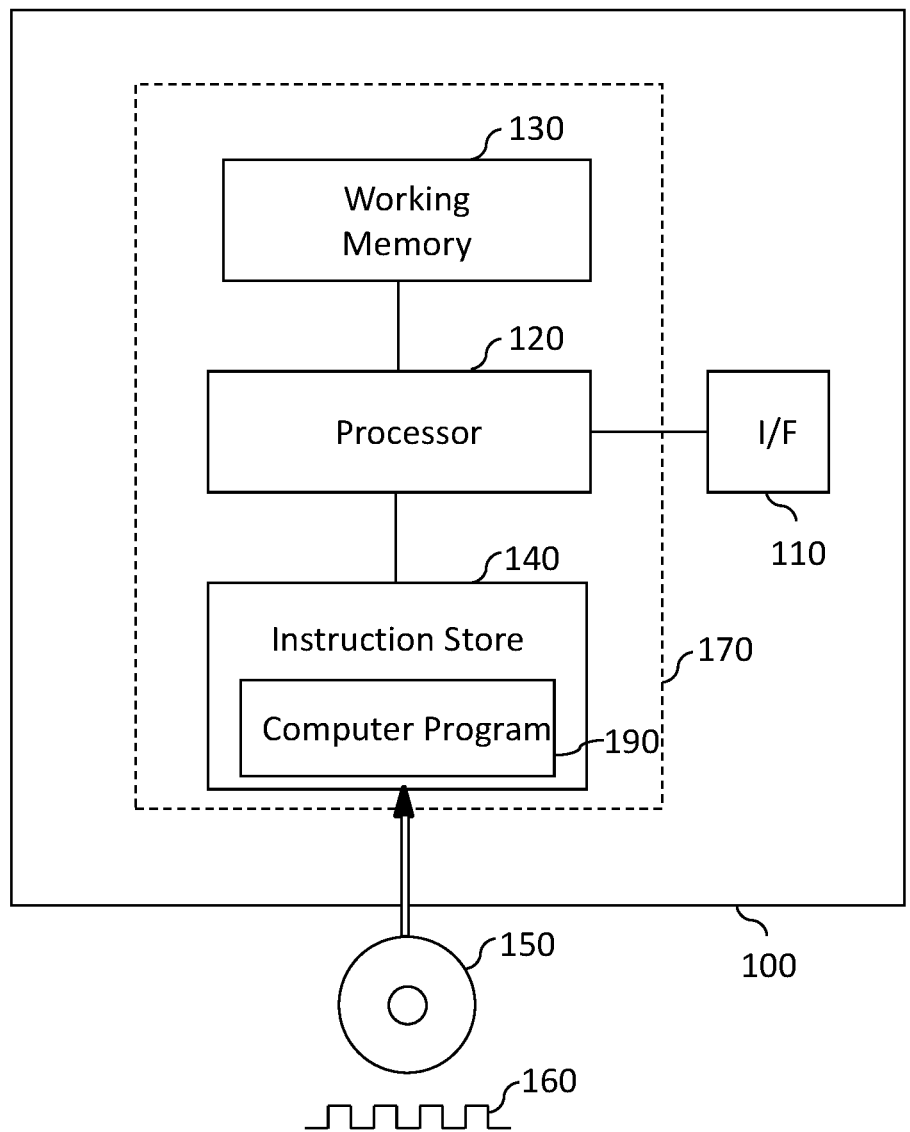
FIG. 4 is a block diagram illustrating an example implementation of the image processing system of the first example embodiment in programmable signal processing hardware.

FIG. 4 is a schematic illustration of a programmable signal processing hardware 100, which may be configured to process OCT image data using the techniques described herein and which can function as the receiver module 2, the A-scan processing module 4 and the mapping module 6 of the first example embodiment.

The programmable signal processing apparatus 100 comprises a communication interface (I/F) 110 for receiving from the OCT imaging device 40, OCT image data representing an OCT image of the retina 20, and outputting mapping data that maps out a predetermined band of the plurality of distinct bands in the OCT image. The signal processing apparatus 100 further comprises a processor (e.g. a Central Processing Unit, CPU, or Graphics Processing Unit, GPU) 120, a working memory 130 (e.g. a random access memory) and an instruction store 140 storing a computer program 190 comprising the computer-readable instructions which, when executed by the processor 120, cause the processor 120 to perform various functions including those of the receiver module 2, the A-scan processing module 4 and the mapping module 6 described herein. The working memory 130 stores information used by the processor 120 during execution of the computer program 190. The instruction store 140 may comprise a ROM (e.g. in the form of an electrically-erasable programmable read-only memory (EEPROM) or flash memory) which is pre-loaded with the computer-readable instructions. Alternatively, the instruction store 140 may comprise a RAM or similar type of memory, and the computer-readable instructions of the computer program 190 can be input thereto from a computer program product, such as a non-transitory, computer-readable storage medium 150 in the form of a CD-ROM, DVD-ROM, etc. or a computer-readable signal 160 carrying the computer-readable instructions. In any case, the computer program 190, when executed by the processor 120, causes the processor 120 to execute a method of processing OCT image data as described herein. It should be noted, however, that the receiver module 2, the A-scan processing module 4 and the mapping module 6 may alternatively be implemented in non-programmable hardware, such as an application-specific integrated circuit (ASIC).

In the present example embodiment, a combination 170 of the hardware components shown in FIG. 4, comprising the processor 120, the working memory 130 and the instruction store 140, is configured to perform functions of the receiver module 2, the A-scan processing module 4 and the mapping module 6 that are described below.

Figure 5:
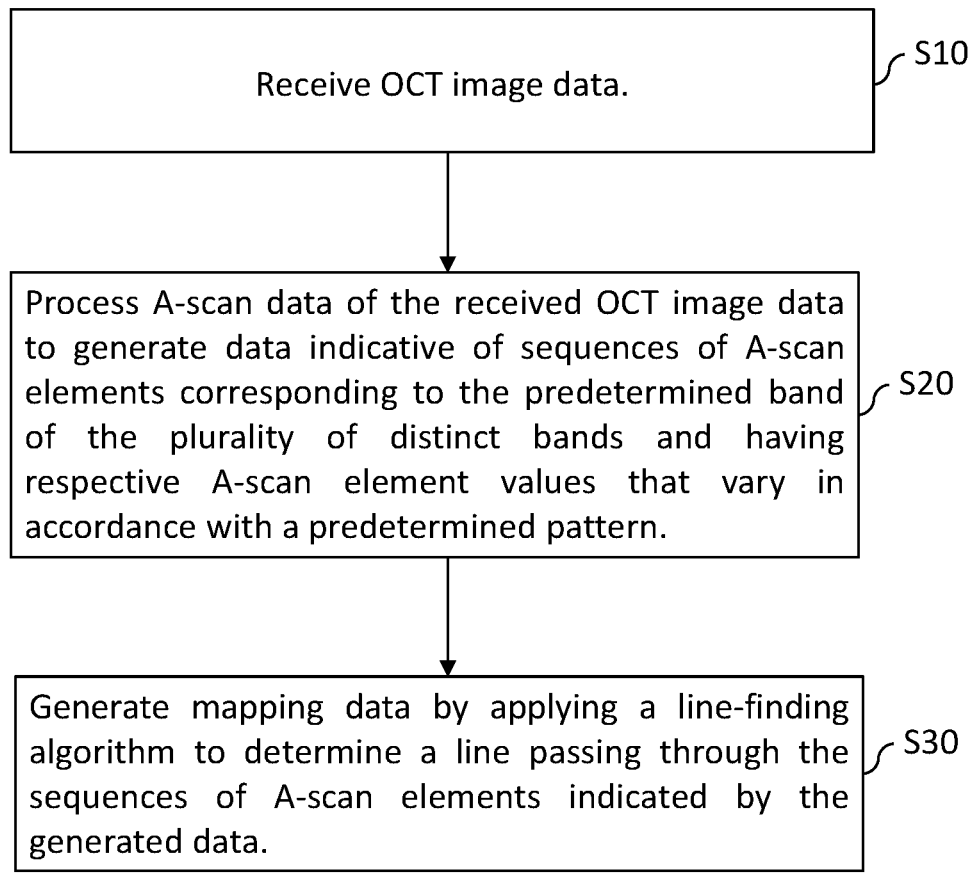
FIG. 5 is a flow diagram illustrating a method of processing OCT image data according to a first example embodiment herein.

FIG. 5 is a flow diagram illustrating a method performed by the image processing apparatus 10 according to the first example embodiment, by which the image processing apparatus 10 processes OCT image data defining an OCT image of at least a portion of the retina 20 to generate mapping data which maps out a predetermined band (e.g. band 92) of a plurality of distinct bands 91, 92 and 93 which extend across the OCT image and correspond to respective anatomical layers of the retina 20. The mapping data may, as in the present example embodiment, comprise a set of coordinate values expressed in a coordinate system of the B-scan (wherein, for example, each coordinate is a pair of identifier values comprising a first identifier value which identifies an A-scan within the B-scan, and a second identifier value which identifies an A-scan element within the A-scan that is identified by the first identifier value), where the coordinate values map out (or trace) the predetermined band across at least a part of the B-scan.

In process S10 of FIG. 5, the receiver module 2 receives OCT image data which, in the present example embodiment, comprises B-scan data that is composed of A-scan data of a plurality of A-scans, as illustrated schematically in FIG. 3.

It should be noted that the receiver module 2 may receive in step S10 B-scan data of a plurality of B-scans (in other words, C-scan data).

In process S20 of FIG. 5, the A-scan processing module 4 processes A-scan data of the OCT image data received in process S10 to generate data indicative of sequences of A-scan elements corresponding to the predetermined one of the plurality of distinct bands and having respective A-scan element values that vary in accordance with a predetermined pattern.

The A-scan processing module 4 may, as in the present embodiment, process the A-scan data of the received OCT image data to generate the data indicative of sequences of A-scan elements corresponding to the predetermined one of the plurality of distinct bands by calculating a cross-correlation of the A-scan data with a kernel which is configured to accentuate sequences of A-scan elements having respective A-scan element values that vary in accordance with the predetermined pattern (in other words, yield a higher cross-correlation value when cross-correlated with sequences of A-scan elements having respective A-scan element values that vary in accordance with the predetermined pattern on which the kernel is based).

Figure 6:
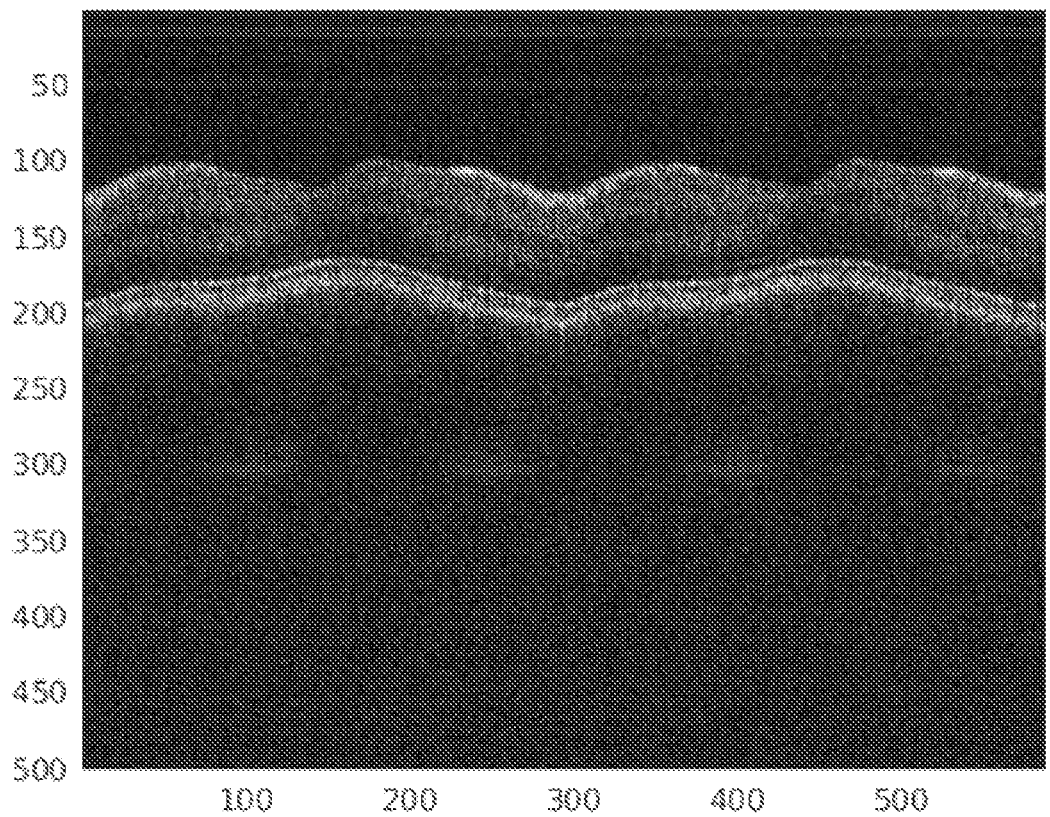
FIG. 6 is an example of an OCT-B scan (OCT image) corresponding to OCT image data acquired by the receiver module in step S10 of FIG. 5.

FIG. 6 illustrates an example of a rendered B-scan corresponding to OCT image data that is received by the receiver module 2 in process S10 according to the first example embodiment. In FIG. 6, each pixel column of the displayed B-scan corresponds to an A-scan that is to be processed by the A-scan processing module 2 in process S20.

Figure 1A:
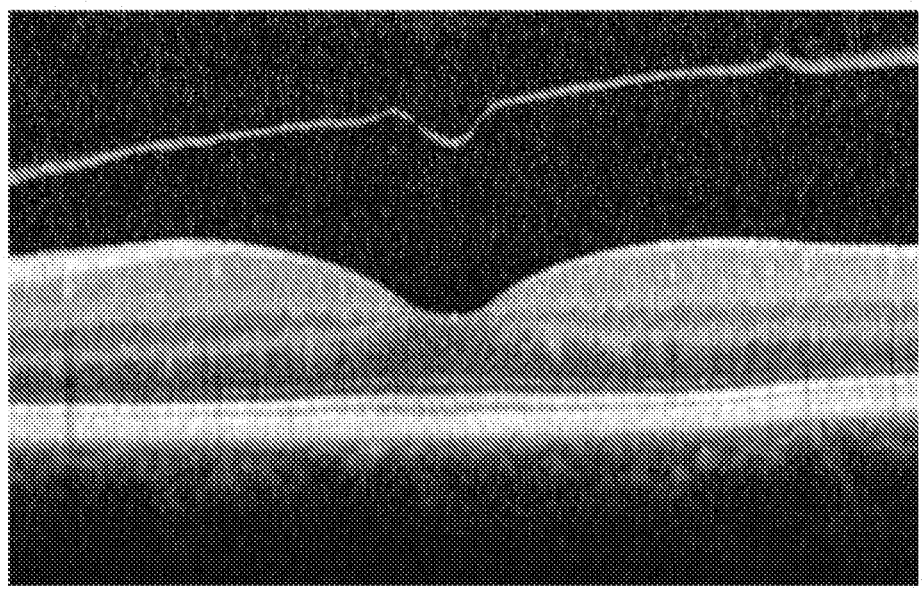
FIG. 1a illustrates an OCT B-scan image of a retina of an eye.
Figure 1B:
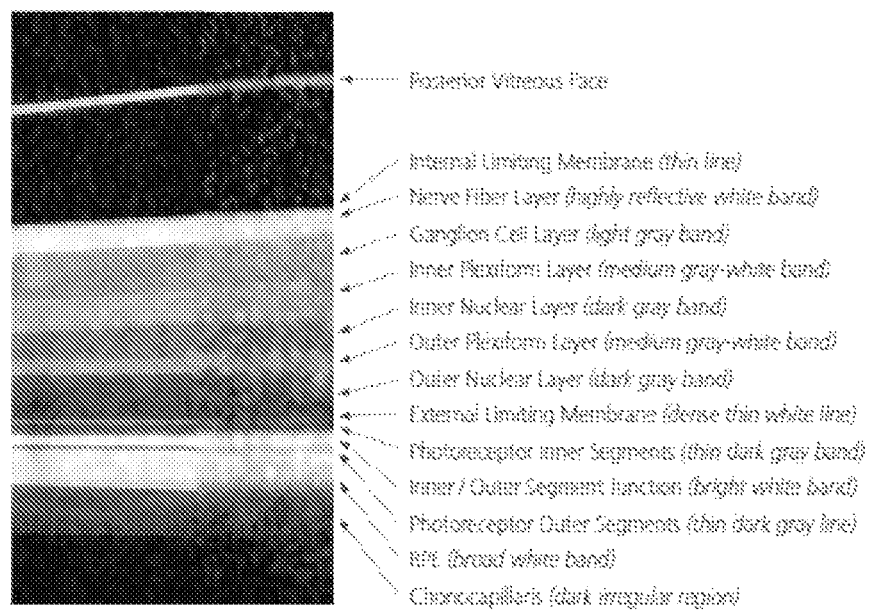

In the present example embodiment, the predetermined band in the B-scan image which is selected to be mapped out is the photoreceptor outer segment of the retina 20. As shown in FIG. 1b, the photoreceptor outer segment of the retina 20 is observed as a relatively dark band between two adjacent lighter bands that are provided on either side of the photoreceptor outer segment, which is the expected intensity variation pattern for the photoreceptor outer segment in a retina. Based on this intensity variation pattern that is representative of the photoreceptor outer segment and its adjacent layers in an OCT image, an appropriate kernel can be selected and cross-correlated with the A-scans of the received OCT image data in order to accentuate sequences of A-scan elements from among the A-scan elements, which sequences of A-scan elements have respective A-scan element values that vary in accordance with the predetermined pattern.

Although the present example embodiment refers to the photoreceptor outer segment as the band to be accentuated (and subsequently mapped out in the B-scan), it should be noted that a different band, corresponding to another retinal layer (e.g. the IS/OS junction layer), may be instead be accentuated by selecting a kernel that is tailored to 'activate' on that band. In particular, the amplitude response of the kernel should be selected based on the (known) variation in intensity of the selected band relative to the adjacent bands in the B-scan image.

In the present example embodiment, in order to enhance the photoreceptor outer segment, the A-scan processing module 4 cross-correlates a one-dimension sine-Gaussian kernel with each sequence of the A-scan data of the OCT image data received by the receiver module 2. The sine-Gaussian kernel is defined as a product of a sine (or cosine wave) having a frequency $\omega$ with a Gaussian function with a standard deviation of $\sigma$. A one-dimensional sine-Gaussian filter can be mathematically represented as:

$$g(x) = \frac{1}{\sqrt{2\pi}\sigma} e^{-\frac{x^2}{2\sigma^2}} \cos(2\pi\omega x) \text{ or} \quad (1)$$

$$g(x) = \frac{1}{\sqrt{2\pi}\sigma} e^{-\frac{x^2}{2\sigma^2}} \sin(2\pi\omega x)$$

Figure 7:
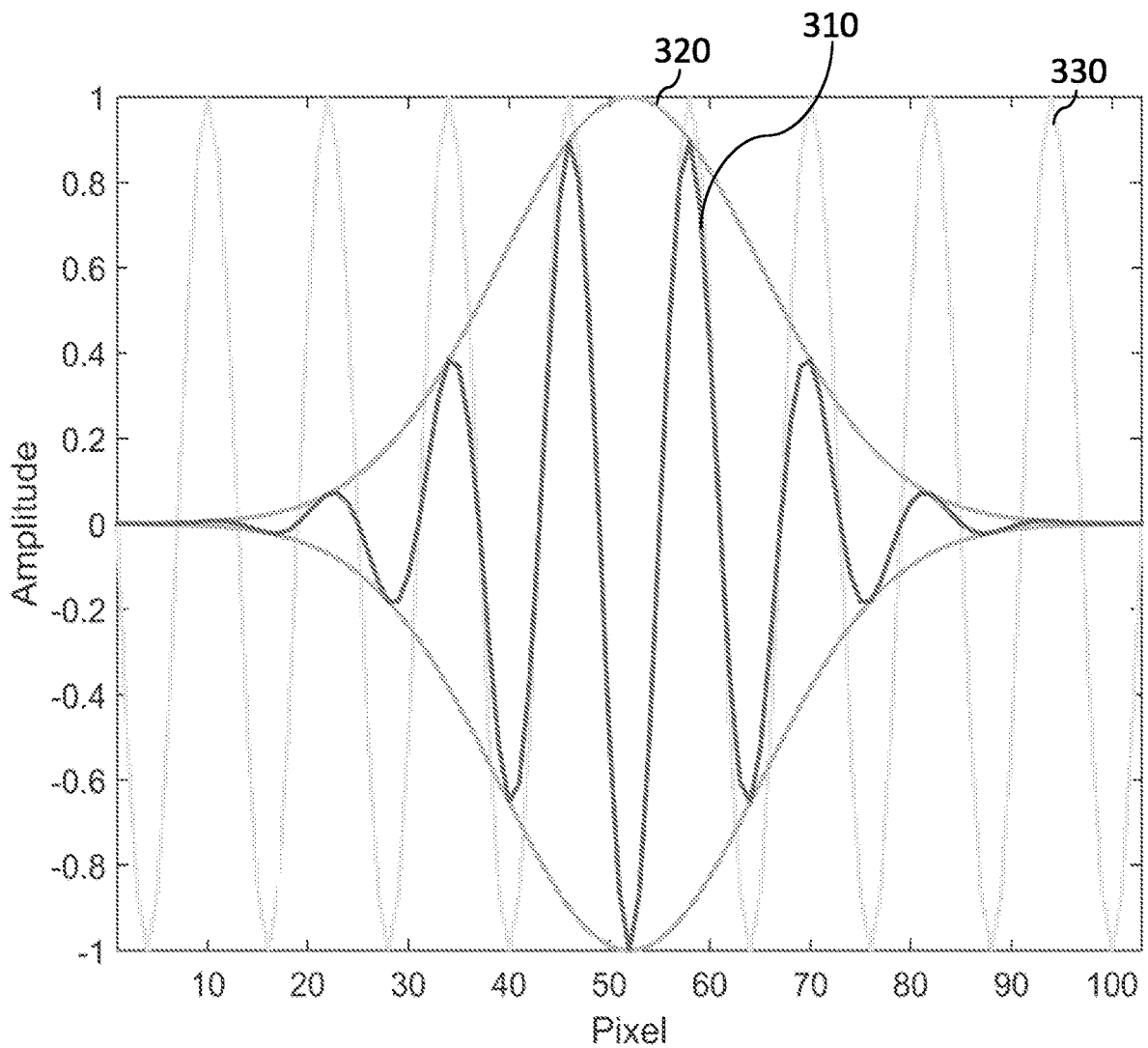
FIG. 7 illustrates the amplitude response of a sine-Gaussian kernel that may be cross-correlated with an A-scan of the received OCT image data to accentuate A-scan elements on the A-scan corresponding to a selected band on the OCT image.

FIG. 7 illustrates a non-limiting example of a sine-Gaussian kernel 310, which is formed by multiplying a sine signal 330 and a Gaussian signal 320. The amplitude of the kernel is plotted as a function of pixel/kernel element index.

The sine-Gaussian kernel may, as in the present embodiment, be a one-dimension kernel. For example, assuming the A-scan data is represented by f(x) and the kernel is represented by g(x), the cross-correlation operation between the A-scan data f(x) and the kernel g(x) to generate correlation output h(t) can be mathematically represented as:

$$h(t) = \Sigma_x f(x) g(x-t) \quad (2)$$

The cross-correlation function thus generates a correlation output h(t) that indicates a degree of similarity between the A-scan data f(x) and shifted copies of the kernel g(x). In this manner, when the sine-Gaussian kernel is cross-correlated with an A-scan of the received OCT image data, a correlation output is generated that accentuates (by yielding a higher value for) sequences of A-scan elements having respective A-scan element values that vary in a similar way to the amplitude response of the kernel. As the kernel is selected based on the band of interest (in particular, based on the variation in pixel intensity of the band of the interest compared to the immediately adjacent bands), the cross-correlation operation accentuates sequences of A-scan elements which from part of the band of interest in the B-scan image.

The amplitude response of the kernel may be selected based on a characteristic of the predetermined band of the plurality of bands that extend across the OCT image. For example, the sine-Gaussian kernel may, as shown in FIG. 7, have a minimum at a central element of the kernel. This is because a maximum correlation response is desired in the middle of the dark layer in the B-can image corresponding to the photoreceptor outer segment. The sine-Gaussian kernel of FIG. 7 also has two equal-sized maxima at either side of the minimum, which ensures that when the sine-Gaussian kernel is cross-correlated with an A-scan of the OCT image data, a maximum correlation response is produced when the minimum is aligned with the middle of the darker layer corresponding to the photoreceptor outer segment and the two maxima are aligned with the respective lighter layers that are on either side of the photoreceptor outer segment (i.e. the inner/outer segment junction on one side of the photoreceptor outer segment, and the RPE on the other side of the photoreceptor outer segment).

In some example embodiments, instead of directly cross-correlating an A-scan with a kernel, the A-scan processing module 4 may alternatively calculate a normalised cross-correlation by first normalizing the A-scan data and the kernel to unit length before cross-correlating the normalised vectors. The normalized cross-correlation between A-scan data f(x) and the kernel g(x) can be expressed as:

$$h(t) = \frac{\Sigma_x [f(x) - \bar{f}][g(x-t) - \bar{g}]}{\sqrt{\Sigma_x [f(x) - \bar{f}]^2 \Sigma_x [g(x-t) - \bar{g}]^2}} \quad (3)$$

wherein $\bar{g}$ is the mean value of the kernel g(x) and $\bar{f}$ is the mean value of the A-scan elements of the A-scan data f(x) overlapping the kernel g(x) for a particular correlation operation. An advantage of calculating a normalised cross-correlation, rather than a direct cross-correlation, is that the calculated normalised cross-correlation value may be affected to a smaller degree by positional variations in energy across the image, for example.

The A-scan processing module 4 may calculate the cross-correlation by cross-correlating each A-scan of the OCT image data with the kernel, in turn, so that, for the number N of A-scans, N separate cross-correlation calculations are performed to generate N respective correlation output vectors, each correlation output vector being a M×1 array of correlation values. The N correlation output vectors can then be rearranged to form a M×N correlation output array.

However, to achieve faster computation of the cross-correlation, the A-scan processing module 4 may, as in the present embodiment, concatenate successive A-scans of the received OCT image data to form concatenated A-scan data, before calculating a cross-correlation between the concatenated A-scan data and the kernel. In the present example embodiment, the A-scan processing module 4 concatenates the N A-scans (each of dimension M×1) to form a MN×1-sized concatenated A-scan data array. The A-scan processing module 4 then calculates a cross-correlation between the concatenated A-scan data array and the kernel to form a MN×1-sized array of correlation values. This array can then be rearranged into N arrays of size M×1, which can be reassembled to form a M×N array referred to herein as a correlation map.

Figure 8:
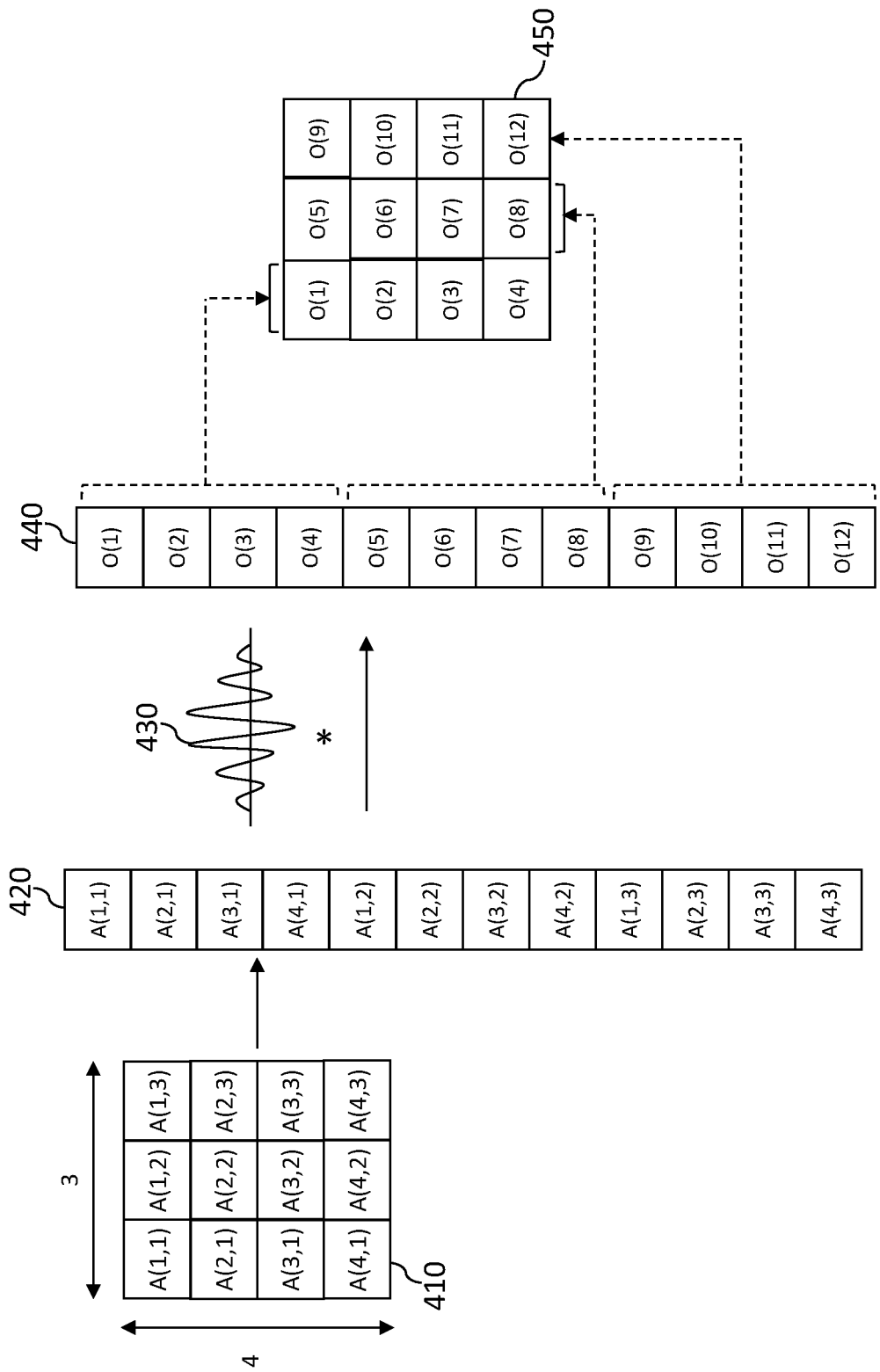
FIG. 8 illustrates a process of concatenating consecutive A-scans and cross-correlating the concatenated A-scan with the kernel, in accordance with an example embodiment.

FIG. 8 illustrates the above described process by which the A-scan processing module 4 calculates the cross-correlation using concatenated A-scans. In FIG. 8, two-dimensional array 410 represents an OCT B-scan image which is formed by three A-scans, each A-scan being a 4×1 element array. The three A-scans are concatenated to form a concatenated A-scan 420, which is represented by a 12×1-element array, so that the last element (A(4, 1)) of the first A-scan (containing elements A(1, 1) to A(4, 1)) precedes the first element (A(1, 2)) of the second A-scan (containing elements A(1, 2) to A(4, 2)), for example. The concatenated A-scan 420 is then cross-correlated with a kernel 430 selected to accentuate specific A-scan elements of the concatenated A-scan 420 that correspond to the predetermined band of interest in the B-scan 410. The cross-correlation operation generates a 12×1-element correlation output vector 440. Finally, the 12×1 correlation output vector 440 is rearranged based on the length of each original A-scan, and rearranged to form a 4×1 correlation value array 450 (also referred to here as a "correlation map"), as shown in FIG. 8.

It should be noted that, although a cross-correlation (or normalized cross-correlation) between the A-scan data and the kernel is calculated in the above examples, in alternative embodiments, a convolution between the A-scan data and the kernel may be calculated instead. That is, the A-scan data of the received OCT image data may be processed to generate the data indicative of the sequences of A-scan elements (that correspond to the predetermined band of the plurality of distinct bands and having respective A-scan element values that vary in accordance with a predetermined pattern) by calculating a convolution of the A-scan data with the kernel that is configured to accentuate sequences of A-scan elements having respective A-scan element values that vary in accordance with the predetermined pattern.

The convolution output h(t) between A-scan data f(x) and kernel g(x) may be written as:

$$h(t) = \Sigma_x f(x) g(t-x) \quad (4)$$

When the kernel is symmetrical (as is the case for the sine-gaussian kernel in the example of FIG. 7, which is substantially symmetrical about a minimum located at a central element of the kernel), the convolution of the A-scan data with the kernel generates the same result as a cross-correlation between the A-scan data and the kernel. Accordingly, either cross-correlation or convolution can be performed as part of step S20, to generate data indicative of sequences of A-scan elements corresponding to the predetermined band of the plurality of distinct bands and having respective A-scan element values that vary in accordance with the predetermined pattern. Furthermore, in some embodiments, normalization may be performed on the A-scan data and the kernel before convolution is performed. In addition, in some embodiments, the convolution may be calculated by concatenating the A-scan data to form concatenated A-scan data and convolving the concatenated A-scan data with the kernel to generate the data indicative of the sequences of A-scan elements. The A-scan data may be concatenated in the same manner as previously described in relation to the example in FIG. 8.

Figure 9:
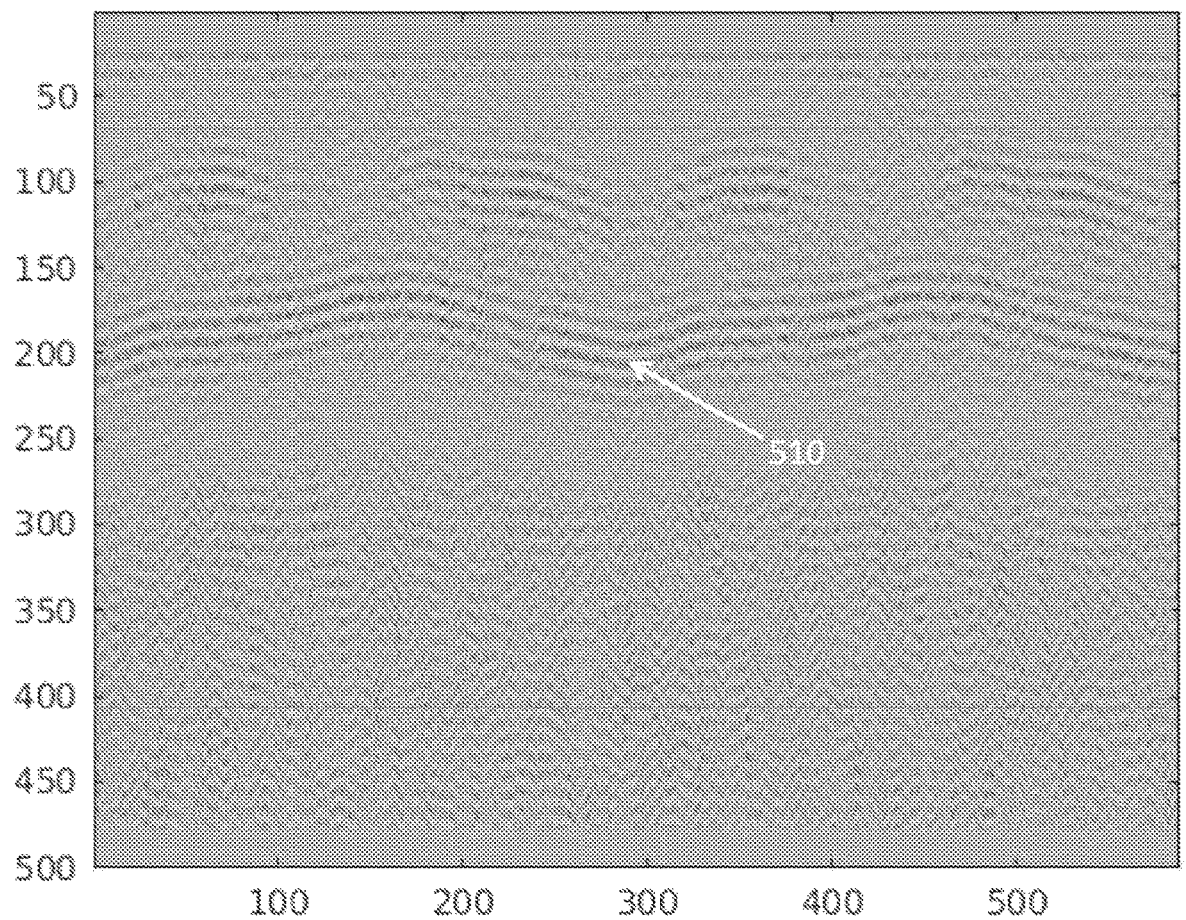
FIG. 9 illustrates a correlation map obtained by cross-correlating the OCT image data for the OCT image of FIG. 6 with a sine-Gaussian kernel.

FIG. 9 shows an example of correlation map calculated by the A-scan processing module 4 as described above, specifically by cross-correlating the A-scans of FIG. 6 with the sine-Gaussian kernel of FIG. 7. The intensity of each pixel in the correlation map is indicative of the correlation value of the correspondingly located element of the correlation value array 450. For the example in FIG. 9, because A-scan elements corresponding to the photoreceptor outer segments are accentuated, higher intensity values are observed at pixels of the correlation map which correspond to A-scan elements representing the photoreceptor outer segment. Label 510 illustrates a region of the correlation map which corresponds to the photoreceptor outer segment.

Although the present example embodiment employs a sine-Gaussian kernel to accentuate the desired band, it should be noted that any kernel capable of accentuating the predetermined pattern corresponding to the band of interest in the B-scan image may alternatively be used. For example, a sine-squared Gaussian kernel (corresponding to a product of a sine-squared function and a Gaussian function) may be used by the A-scan processing module 4 in its cross-correlation calculation to accentuate the photoreceptor outer segment, as the amplitude response of the sine-squared Gaussian waveform substantially follows the intensity variation exhibited by a darker band between two light bands (as is the case with the photoreceptor outer segment).

Furthermore, it should be noted that, although a one-dimensional kernel is used by the A-scan processing module 4 in the present example embodiment to calculate a one-dimensional correlation with the A-scan data, the present invention is not limited to this. For example, in an alternative embodiment, the A-scan processing module 4 may cross-correlate B-scan data of the received OCT image data with a two-dimensional kernel to accentuate sequences of A-scans in adjacent B-scans or C-scans which correspond to the retinal layer of interest.

It should also be noted that, although the A-scan processing module 4 of the present example embodiment accentuates a predetermined band in the B-scan image through the calculation of a cross-correlation of the A-scans with a kernel, the data indicative of sequences of A-scan elements corresponding to the predetermined band and having respective A-scan element values that vary in accordance with a predetermined pattern, may be generated in other ways. For example, in another example embodiment, the A-scan processing module 4 may process the A-scan data of the received OCT image data by using a feature enhancing algorithm to enhance sequences of A-scan elements having respective A-scan element values that vary in accordance with the predetermined pattern corresponding to the predetermined band in the B-scan image. Any other feature detection method may alternatively be used to enhance the predetermined band of interest in the B-scan image.

Referring again to FIG. 5, in process S30, the mapping module 6 generates the mapping data by applying a line-finding algorithm to determine a line passing through the sequences of A-scan elements indicated by the generated data.

For example, in the present example embodiment, after calculating a cross-correlation of the A-scans with the kernel to obtain the correlation map that is formed by a two-dimensional array of correlation values, the mapping module 6 applies a line-finding algorithm to the correlation map to determine the 'strongest' line passing laterally through at least a portion of the correlation map, the 'strongest' line being, for example, a line having an associated highest total correlation value. More specifically, the total correlation value for a line through the correlation map is obtained by summing the correlation values associated with each coordinate position which the line passes through. Furthermore, the estimation of the 'strongest' line is constrained by rules defining an allowed change in Y-coordinate as the X-axis coordinate value of the line is incremented during the mapping process. For example, in the present example embodiment, it is assumed that, as the line progresses from left to right in the correlation map, for each increment of the X-axis value of the line, the Y-axis value of the line may either increment by one unit, decrement by one unit, or remain at its current value. However, the range and size of the Y-value transitions are not limited to these three example transitions, and may be different in other example embodiments.

As the cross-correlation calculation performed by the A-scan processing module 4 has the effect of accentuating the predetermined band of interest in the correlation map, the 'strongest' line through the correlation map, which is determined by the mapping module 6, will consequently tend to pass through the predetermined band.

The mapping module 6 may, as in the present example embodiment, apply the Viterbi algorithm to map out the predetermined band of the OCT image. The Viterbi algorithm may provide an efficient method of determining the most probable set of states, based on a sequence of observations in a Hidden Markov model that has a discrete number of states for each step of the sequence. For a Hidden Markov Model that has M possible states and a sequence length of N, there are $M^N$ possible state sequences. However the Viterbi algorithm does not compute the probability of every possible path, and instead maximises the posterior probability after each discrete step. This means only a fraction of all possible paths need to be computed, so that the Viterbi algorithm's time complexity is only $O(M^2N)$.

In the article "Generalized application of the Viterbi algorithm to searches for continuous gravitational-wave signals" by J. Bayley et al., Phys. Rev. D, Vol. 100, Issue 2 (Jul. 15, 2019), the contents of which are incorporated herein by reference in their entirety, the Viterbi algorithm is used for a different purpose to search for continuous gravitational-wave signals in the time-frequency plane. However, the present inventor has realised that the Viterbi algorithm can also be applied in the present field to identify the strongest line passing laterally through the correlation map, constrained upon predefined trajectory transitions for the line. Although the mapping module 6 employs a Viterbi algorithm to generate the mapping data in the present example embodiment, it should be noted that other types of line-finding algorithms may alternatively be used.

In the present embodiment, the mapping module 6 may apply the Viterbi algorithm to determine the strongest line passing through the two-dimensional correlation map, by taking the correlation values for each coordinate of the correlation map, to indicate the likelihood of the line passing through that particular coordinate. The mapping module 6 may then then calculate the probability of the most probable path ending at each coordinate in the correlation map.

More specifically, for a M×N-element correlation map, the X-axis coordinates j=0, 1, . . . N−1 of the correlation map can be considered to represent each step of the sequence in an underlying Markov process, while each state of the Markov process is represented by the Y-coordinate $y_j$. The coordinates of the correlation map therefore correspond to nodes on a Trellis diagram for the Markov process. A path in the present example embodiment is therefore a list of Y-axis coordinates y={$y_j$}, where $y_j$ is the Y-axis value for coordinate j of the X-axis.

A pseudocode of the Viterbi algorithm, which is used by the mapping module 6 of the present example embodiment to map out the desired band in a retinal B-scan, is set out in Algorithm 1 below.

| [ALGORITHM 1] |
| --- |
| 1: Input: C, T |
| 2: Output: ŷ, V, B |
| 3: |
| 4: INITIALIZATION |
| 5: for Y − coordinate $y_{0,k}$, k = 0 → M − 1 do |
| 6:    $V_{0,k} = C_{0,k}$ |
| 7:    $B_{0,k} = 0$ |
| 8: end for |
| 9: |
| 10: ITERATION |
| 11: for X − coordinate, j = 0 → N − 1 do |
| 12:    for ($y_{j,k}$), k = 0 → M − 1 do |
| 13:      $V_{j,k} = \max_i (C_{j,k} + T_i + V_{j-1,k+i})$, i = −1, 0, 1 |
| 14:      $B_{j,k} = \text{argmax}_i (C_{j,k} + T_i + V_{j-1,k+i})$ |
| 15:    end for |
| 16: end for |
| 17: |
| 18: IDENTIFICATION |
| 19:    $\hat{y}_{N-1} = \text{argmax}_k (V_{N-1,k})$ |
| 20: for X − coordinate, j = N − 1 → 0 do |
| 21:    $\hat{y}_j = \hat{y}_{j+1} + B_{j,k+1}$ |
| 22: end for |

As shown in Algorithm 1, the algorithm divides into three main stages: initialization, iteration and identification. For the present example embodiment, during the iteration stage, the maximisations are performed over i=−1, 0, 1 corresponding to the three possible transitions from each current state. For example, i=−1 refers to a downward transition in Y-coordinate value when stepping to the next X-axis value, i=0 refers to a central transition (no change in Y-coordinate), while i=0 refers to an upward transition in state.

As an input to Algorithm 1, a likelihood matrix C defining likelihood values for each coordinate of the correlation map is first defined. For the present example embodiment, the likelihood matrix C is set using the correspondingly located values of the correlation map. In other words, the likelihood value $C_{j,k}$ is given by the value of the correlation output map at coordinate position (j, k). In the present context, $C_{j,k}$ represents the likelihood of Y-coordinate being k when X-coordinate is j.

The mapping module 6 may, as in the present example embodiment, further define a transition matrix T that stores prior probabilities $p(y_j|y_{j-1})$. For the present example embodiment, it is assumed that a path through correlation map is only allowed to transition by one Y-axis coordinate (corresponding to a state) when stepping from one X-axis value to the next. In other words, the change in Y-value is restricted to an up transition (i.e., the Y-value increases by one), a center transition (the Y-value does not change) or a down transition (Y-value decreases by one). The three values of the transition matrix may be selected to have three values that correspond to three prior probabilities that the path was in the corresponding up, center or down Y-value state at the previous X-coordinate. In the present example embodiment, the strongest line passing through the correlation map is expected to extend from left to right on the map in a horizontal manner, and therefore the "center" transition may be assigned a larger weight than the "up" and "down" transitions. Different values may be selected for the transition matrix T based on prior assumptions of the likelihood of state changes. Furthermore, the transition matrix T may be selected to be of a different dimension, depending on the number of possible transitions from a previous state.

As an output, the Viterbi algorithm herein returns ŷ, which corresponds to the coordinates of the most probable path passing laterally through the correlation map. Matrix V stores the probabilities of the most probable path ending in each coordinate position (j, k) on the correlation map. Matrix B stores the transitions (i.e. changes in Y value) when stepping from one X-axis coordinate to the next.

Figure 10:
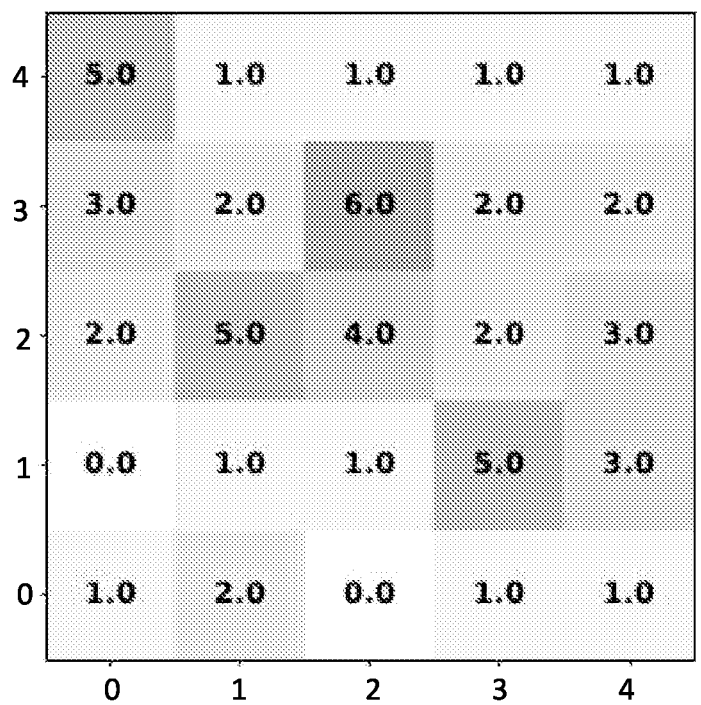
FIG. 10 illustrates an example of a correlation map represented by a two dimensional array of correlation values.

As an example, FIG. 10 is diagram taken from the aforementioned article by J. Bayley et al. which, in the present context, may be taken to represent a 5×5-element correlation map. The pixel value for each coordinate on the correlation map indicates the correlation value for that coordinate. A likelihood matrix C is defined for the correlation map of FIG. 10, wherein each likelihood value $C_{j,k}$ of the likelihood matrix C is assigned the corresponding correlation value for coordinate (j, k) of the correlation map.

Figure 11:
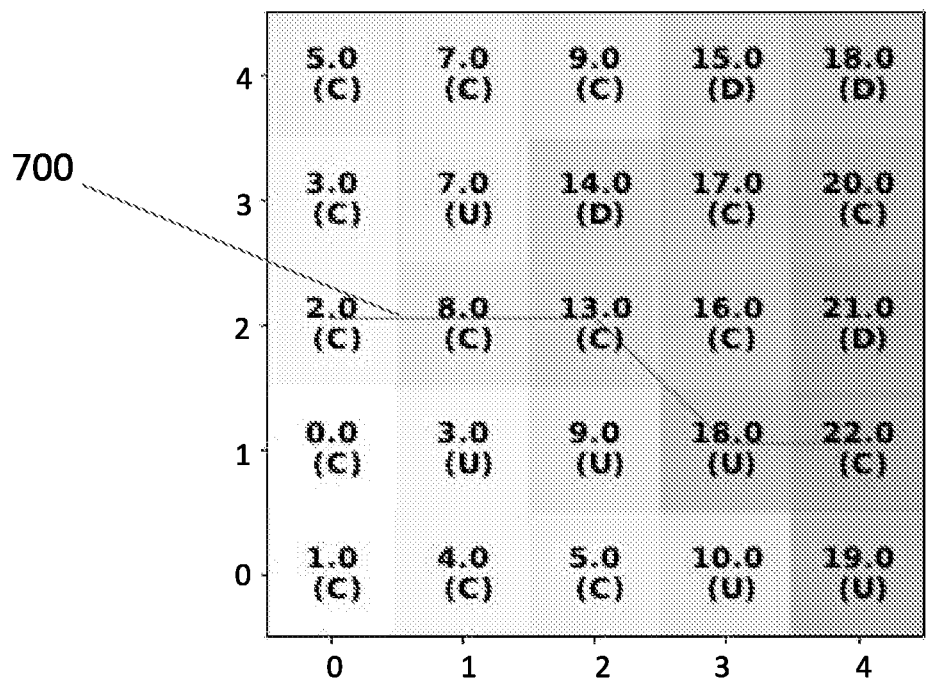
FIG. 11 illustrates a line estimated from the correlation map of FIG. 10 based on the correlation values for each coordinate position in FIG. 10, wherein, in one example embodiment herein, the line is obtained by processing the correlation values of the correlation map in FIG. 10 using a Viterbi algorithm.

FIG. 11 is also a diagram taken from the aforementioned article by J. Bayley et al., which for the present example, can be viewed as a graphical illustration of the various outputs of the Viterbi algorithm. The numeral value within each pixel of the 5×5 array in FIG. 11 denotes the calculated probability $V_{j,k}$ for coordinate (j, k). The transition value $B_{j,k}$ is shown in parenthesis for each pixel, and comprises one of labels, "U" (up), "C" (center), "D" (down) corresponding to i=[−1, 0, 1] respectively.

For the initialization stage of Algorithm 1, the $V_{0,k}$ values of the first column of FIG. 9 are assigned using the corresponding $C_{0,k}$ values in the first column of FIG. 8. The $B_{0,k}$ values are all set to zero (represented by "C" in parenthesis in FIG. 9), as there is no previous transition in this case.

For the iteration stage of the Viterbi algorithm, the algorithm calculates the most probable path that ends at each coordinate (j, k) by calculating $V_{j,k}$ for each coordinate position in the second to fifth columns of FIG. 11. Intuitively, the calculation of $V_{j,k}$ for coordinate (j, k) is obtained based on a maximization of the value $C_{j,k}+T_i+V_{j-1, k+i}$ over i, the three closest coordinates in the previous column. The transition giving the maximum probability is then saved to $B_{j,k}$. The transition yielding the highest probability value is shown in parenthesis in FIG. 11, where "U", "C", "D" correspond to values of i=[−1, 0, 1] respectively. For the example illustrated in FIG. 11, the transition matrix T is selected to be [0, 1, 0] for the up, center and down transitions respectively. However, the dimension and values of the transition matrix T are not limited to this specific example and can be selected as appropriate.

As an example, in FIG. 11, $V_{2,2}$ is calculated by selecting the maximum value from three computed values, $C_{2,2}+T_{-1}+V_{1,1}=7$, $C_{2,2}+T_0+V_{1,2}=13$ and $C_{2,2}+T_1+V_{1,3}=11$. In this example, i=0 (corresponding to a "center" transition) yielded the maximum value, and this transition is therefore stored as $B_{2,2}$. A label "C" is therefore assigned to the coordinate (2,2).

For the identification stage of the algorithm, the most probable path is identified using the calculated $V_{j,k}$ values and the obtained $B_{j,k}$ values. More specifically, the highest probability value in the final column, $$\max_k(V_{N-1,k}),$$

is first identified. The path which corresponds to this highest probability is then traced backwards from right to left on FIG. 11. For example, in FIG. 11, the highest $V_{j,k}$ in the final column is for the coordinate (j, k)=(4,1), and the $B_{j,k}$ value for this coordinate is "C". This indicates that the most probable path in the previous column is provided by the center coordinate of the three coordinates neighbouring the present coordinate. Accordingly, in the present example embodiment, the most probable path in column 3 is at coordinate (3, 1). For the coordinate (3, 1), the stored $B_{3,1}$ value is "U" which indicates that the most probable path in the previous column is provided by the upper coordinate of the three closest coordinates. Accordingly, the most probable path in column 2 is (2, 2). This trace-back process continues until the first column is reached. The retraced coordinates are then taken to indicate the most probable path through the correlation map.

Figure 12:
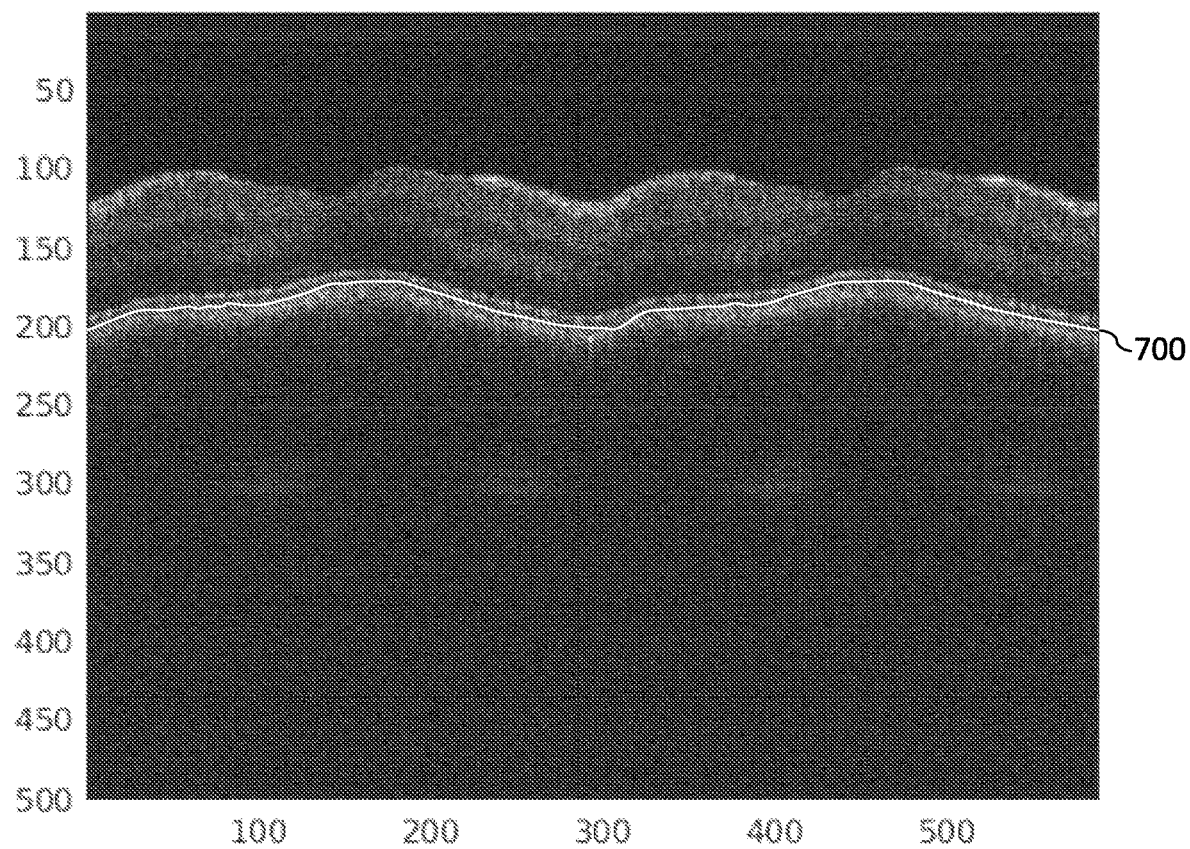
FIG. 12 illustrates the OCT image of FIG. 6, having overlaid therein a line which maps out a selected band of the OCT image, which has been determined by applying the Viterbi algorithm to the correlation map of FIG. 10.

FIG. 12 illustrates the example of the B-scan of FIG. 6, having overlaid thereon a line 700, which passes through the band corresponding to the photoreceptor outer segment. The line 700 is defined by the mapping data, which has been generated by the mapping module 6 applying the Viterbi algorithm described above to the correlation map generated by the A-scan processing module 4.

It should be noted that although a line-finding algorithm is applied to a correlation map in the foregoing examples, the line-finding algorithm can alternatively be applied to a convolution map obtained by convolving the A-scan data with the kernel, in embodiments where the A-scan data is convolved with the kernel to generate the data indicative of sequences of A-scan elements corresponding to the predetermined band of the plurality of distinct bands and having respective A-scan element values that vary in accordance with the predetermined pattern. More generally, it should be understood that any of the previously described examples that employ cross-correlation can alternatively be implemented using convolution, when the kernel that is used to accentuate the sequences of A-scan elements is symmetrical or substantially symmetrical.

The example aspects described herein avoid limitations, specifically rooted in computer technology, relating to conventional techniques for conducting image scanning in optical scanning environments. For example, the use of known image classification algorithms, such as CNN based segmentation, to segment OCT retinal images into distinct retinal layers, can involve slow, resource-intensive training (and possible re-training, particularly if different imaging systems are used). The techniques described herein, on the other hand, enable automatic mapping of one or more retinal layers in an OCT retinal image to be accomplished substantially faster and in a more computationally efficient manner, using less computer processing and memory resources, relative to the conventional techniques. Also, by virtue of the foregoing capabilities of the example aspects described herein, which are rooted in computer technology, the example aspects described herein improve computers and computer processing/functionality, and also improve the field(s) of at least image processing, OCT, and data processing, and the processing of functional image data.

In the foregoing description, example aspects are described with reference to several example embodiments. Accordingly, the specification should be regarded as illustrative, rather than restrictive. Similarly, the figures illustrated in the drawings, which highlight the functionality and advantages of the example embodiments, are presented for example purposes only. The architecture of the example embodiments is sufficiently flexible and configurable, such that it may be utilised (and navigated) in ways other than those shown in the accompanying figures.

Software embodiments of the examples presented herein may be provided as, a computer program, or software, such as one or more programs having instructions or sequences of instructions, included or stored in an article of manufacture such as a machine-accessible or machine-readable medium, an instruction store, or computer-readable storage device, each of which can be non-transitory, in one example embodiment (and can form a memory or store). The program or instructions on the non-transitory machine-accessible medium, machine-readable medium, memory, instruction store, or computer-readable storage device or medium, may be used to program a computer system or other electronic device. The machine- or computer-readable device/medium, memory, instruction store, and storage device may include, but are not limited to, floppy diskettes, optical disks, and magneto-optical disks or other types of media/machine-readable medium/instruction store/storage device suitable for storing or transmitting electronic instructions. The techniques described herein are not limited to any particular software configuration. They may find applicability in any computing or processing environment. The terms "computer-readable medium", "machine-accessible medium", "machine-readable medium", "memory", "instruction store", "computer-readable storage medium", and "computer-readable storage device" used herein shall include any medium that is capable of storing, encoding, or transmitting instructions or a sequence of instructions for execution by the machine, computer, or computer processor and that causes the machine/computer/computer processor to perform any one of the methods described herein. Furthermore, it is common in the art to speak of software, in one form or another (e.g., program, procedure, process, application, module, unit, logic, and so on), as taking an action or causing a result. Such expressions are merely a shorthand way of stating that the execution of the software by a processing system causes the processor to perform an action to produce a result.

Some embodiments may also be implemented by the preparation of application-specific integrated circuits, field-programmable gate arrays, or by interconnecting an appropriate network of conventional component circuits.

Some embodiments include a computer program product. The computer program product may be a storage medium or media, memory, instruction store(s), or storage device(s), having instructions stored thereon or therein which can be used to control, or cause, a computer or computer processor to perform any of the procedures of the example embodiments described herein. The storage medium/memory/instruction store/storage device may include, by example and without limitation, an optical disc, a ROM, a RAM, an EPROM, an EEPROM, a DRAM, a VRAM, a flash memory, a flash card, a magnetic card, an optical card, nanosystems, a molecular memory integrated circuit, a RAID, remote data storage/archive/warehousing, and/or any other type of device suitable for storing instructions and/or data.

Stored on any one of the computer-readable medium or media, memory, instruction store(s), or storage device(s), some implementations include software for controlling both the hardware of the system and for enabling the system or microprocessor to interact with a human user or other mechanism utilizing the results of the example embodiments described herein. Such software may include without limitation device drivers, operating systems, and user applications. Ultimately, such computer-readable media or storage device(s) further include software for performing example aspects of the invention, as described above.

Included in the programming and/or software of the system are software modules for implementing the procedures described herein. In some example embodiments herein, a module includes software, although in other example embodiments herein, a module includes hardware, or a combination of hardware and software.

While various example embodiments of the present invention have been described above, it should be understood that they have been presented by way of example, and not limitation. It will be apparent to persons skilled in the relevant art(s) that various changes in form and detail can be made therein. Thus, the present invention should not be limited by any of the above described example embodiments, but should be defined only in accordance with the following claims and their equivalents.

Further, the purpose of the Abstract is to enable the Patent Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the example embodiments presented herein in any way. It is also to be understood that any procedures recited in the claims need not be performed in the order presented.

While this specification contains many specific embodiment details, these should not be construed as limitations on the scope of any inventions or of what may be claimed, but rather as descriptions of features specific to particular embodiments described herein. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Having now described some illustrative embodiments and embodiments, it is apparent that the foregoing is illustrative and not limiting, having been presented by way of example. The devices and apparatus described herein may be embodied in other specific forms without departing from the characteristics thereof. The foregoing embodiments are illustrative rather than limiting of the described systems and methods. Scope of the OCT data processing methods and apparatuses described herein is thus indicated by the appended claims, rather than the foregoing description, and changes that come within the meaning and range of equivalence of the claims are embraced therein.

The invention claimed is:

1. A method of processing optical coherence tomography, OCT, image data representing an OCT image of a retina of an eye, to generate mapping data which maps out a predetermined band of a plurality of distinct bands which extend across the OCT image and correspond to respective anatomical layers of the retina, the method comprising:
receiving the OCT image data;
processing A-scan data of the received OCT image data to generate a resulting map indicative of sequences of A-scan elements corresponding to the predetermined band of the plurality of distinct bands and having respective A-scan element values that vary in accordance with a predetermined pattern, wherein the processing includes:
selecting a kernel based on the predetermined band, and
calculating values of one of a cross-correlation or a convolution of the A-scan elements with the kernel to generate the resulting map; and
generating the mapping data by applying a line-finding algorithm to the resulting map obtained in the calculating to determine a line passing through the sequences of A-scan elements indicated by the resulting map, based on values of coordinates of the resulting map, wherein the line has an associated total value which is higher than total values of other lines passing through the resulting map, the total value of each line being a sum of calculated values associated with coordinate positions through which the line passes.

2. The method according to claim 1, wherein, in the selecting, the kernel is selected based on a variation of A-scan element values of the predetermined band compared to A-scan element values in immediately adjacent bands of the plurality of distinct bands, the kernel being configured to accentuate sequences of A-scan elements having respective A-scan element values that-vary in accordance with the predetermined pattern.

3. The method according to claim 2, wherein the kernel is one of a sine Gaussian kernel and a sine-squared Gaussian kernel.

4. The method according to claim 2, further comprising concatenating the A-scan data to form a one-dimensional array of concatenated A-scan data, wherein the calculating is performed by calculating values of one of a cross-correlation or a convolution between the one-dimensional array of concatenated A-scan data and the kernel to generate the resulting map.

5. The method according to claim 1, wherein the A-scan data of the received OCT image data is processed to generate the resulting map indicative of the sequences of A-scan elements by using a feature enhancing algorithm to enhance A-scan elements belonging to respective sequences of A-scan elements whose A-scan element values vary in accordance with the predetermined pattern.

6. The method according to claim 1, wherein the line-finding algorithm comprises a Viterbi algorithm.

7. The method according to claim 1, wherein the predetermined one of the plurality of distinct bands corresponds to one of an inner segment/outer segment junction layer of the retina and a photoreceptor outer segment of the retina.

8. The method according to claim 1, wherein the received OCT image data comprises one of OCT B-scan data and OCT C-scan data.

9. The method according to claim 1, wherein the calculating is performed by calculating values of one of a cross-correlation or a convolution of a normalized version of the A-scan elements with a normalized version of the kernel to generate the resulting map.

10. The method according to claim 9, further comprising normalizing the A-scan elements and the kernel.

11. An image processing apparatus configured to process optical coherence tomography, OCT, image data representing an OCT image of a retina of an eye, to generate mapping data which maps out a predetermined band of a plurality of distinct bands which extend across the OCT image and correspond to respective anatomical layers of the retina, the apparatus comprising:
receiver module configured to receive the OCT image data;
an A-scan processing module configured to process A-scan data of the received OCT image data to generate a resulting map indicative of sequences of A-scan elements corresponding to the predetermined band of the plurality of distinct bands and having respective A-scan element values that vary in accordance with a predetermined pattern, by:
selecting a kernel based on the predetermined band; and
calculating values of one of a cross-correlation or a convolution of the A-scan elements with the kernel to generate the resulting map; and
a mapping module configured to generate the mapping data by applying a line-finding algorithm to the resulting map obtained in the calculating to determine a line passing through the sequences of A-scan elements indicated by the resulting map, based on values of coordinates of the resulting map, wherein the line has an associated total value which is higher than total values of other lines passing through the resulting map, the total value of each line being a sum of calculated values associated with coordinate positions through which the line passes.

12. The image processing apparatus according to claim 11, wherein in the selecting, the a kernel is selected based on a variation of A-scan element values of the predetermined band compared to A-scan element values in immediately adjacent bands of the plurality of distinct bands, the kernel being configured to accentuate sequences of A-scan elements having respective A-scan element values that vary in accordance with the predetermined pattern.

13. The image processing apparatus according to claim 12, wherein the kernel is one of a sine-Gaussian kernel and a sine-squared Gaussian kernel.

14. The image processing apparatus according to claim 12, wherein the A-scan processing module also is configured to concatenate the A-scan data to form a one-dimensional array of concatenated A-scan data, and performs the calculating by calculating values of one of a cross-correlation or a convolution between the one-dimensional array of concatenated A-scan data and the kernel to generate the resulting map.

15. The image processing apparatus according to claim 11, wherein the A-scan processing module is configured to process the A-scan data of the received OCT image data to generate the resulting map indicative of the sequences of A-scan elements by using a feature enhancing algorithm to enhance A-scan elements belonging to respective sequences of A-scan elements whose A-scan element values vary in accordance with the predetermined pattern.

16. The image processing apparatus according to claim 11, wherein the line-finding algorithm comprises a Viterbi algorithm.

17. The image processing apparatus according to claim 11, wherein the predetermined one of the plurality of distinct bands corresponds to one of an inner segment/outer segment junction layer of the retina and a photoreceptor outer segment of the retina.

18. The image processing apparatus according to claim 11, wherein the receiver module is configured to receive, as the OCT image data, at least one of OCT B-scan data comprising the A-scan data or OCT C-scan data comprising the A-scan data.

19. The image processing apparatus according to claim 11, wherein the calculating is performed by calculating values of one of a cross-correlation or a convolution of a normalized version of the A-scan elements with a normalized version of the kernel to generate the resulting map.

20. The image processing apparatus method according to claim 19, wherein the A-scan processing module is further configured to normalize the A-scan elements and the kernel.

21. A non-transitory computer-readable storage medium storing computer program instructions which, when executed by a computer, cause the computer to perform a method of processing optical coherence tomography, OCT, image data representing an OCT image of a retina of an eye, to generate mapping data which maps out a predetermined band of a plurality of distinct bands which extend across the OCT image and correspond to respective anatomical layers of the retina, the method comprising:
receiving the OCT image data;
processing A-scan data of the received OCT image data to generate a resulting map indicative of sequences of A-scan elements corresponding to the predetermined band of the plurality of distinct bands and having respective A-scan element values that vary in accordance with a predetermined pattern, wherein the processing module includes:
selecting a kernel based on the predetermined band; and
calculating values of one of a cross-correlation or a convolution of the A-scan elements with the kernel to generate the resulting map; and
generating the mapping data by applying a line-finding algorithm to the resulting map obtained in the calculating to determine a line passing through the sequences of A-scan elements indicated by the resulting map, based on values of coordinates of the resulting map, wherein the line has an associated total value which is higher than total values of other lines passing through the resulting map, the total value of each line being a sum of calculated values associated with coordinate positions through which the line passes.

22. The non-transitory computer-readable storage medium according to claim 21, wherein in the selecting, the kernel is selected based on a variation of A-scan element values of the predetermined band compared to A-scan element values in immediately adjacent bands of the plurality of distinct bands, the kernel being configured to accentuate sequences of A-scan elements having respective A-scan element values that vary in accordance with the predetermined pattern.

23. The non-transitory computer-readable storage medium according to claim 22, wherein the kernel is one of a sine Gaussian kernel and a sine-squared Gaussian kernel.

24. The non-transitory computer-readable storage medium according to claim 22, wherein the computer program, when executed by the computer, also causes the computer to concatenate the A-scan data to form a one-dimensional array of concatenated A-scan data, and wherein the calculating is performed by calculating values of one of a cross-correlation and a convolution between the one-dimensional array of concatenated A-scan data and the kernel.

25. The non-transitory computer-readable storage medium according to claim 21, wherein the computer program, when executed by the computer, causes the computer to process the A-scan data of the received OCT image data to generate the resulting map indicative of the sequences of A-scan elements by using a feature enhancing algorithm to enhance A-scan elements belonging to respective sequences of A-scan elements whose A-scan element values vary in accordance with the predetermined pattern.

26. The non-transitory computer-readable storage medium according to claim 21, wherein the line-finding algorithm comprises a Viterbi algorithm.

27. The non-transitory computer-readable storage medium according to claim 21, wherein the predetermined band of the plurality of distinct bands corresponds to one of an inner segment/outer segment junction layer of the retina and a photoreceptor outer segment of the retina.

28. The non-transitory computer-readable storage medium according to claim 21, wherein the received OCT image data comprises one of OCT B-scan data and OCT C-scan data.

29. The non-transitory computer-readable storage medium according to claim 21, wherein the calculating is performed by calculating values of one of a cross-correlation or a convolution of a normalized version of the A-scan elements with a normalized version of the kernel to generate the resulting map.

30. The non-transitory computer-readable storage according to claim 29, wherein the processing further comprises normalizing the A-scan elements and the kernel.

* * * * *